US010757975B2

(12) United States Patent
Batista et al.

(10) Patent No.: US 10,757,975 B2
(45) Date of Patent: Sep. 1, 2020

(54) AEROSOL-GENERATING SYSTEM COMPRISING A REMOVABLE HEATER

(71) Applicant: Philip Morris Products S.A., Neuchatel (CH)

(72) Inventors: Rui Nuno Batista, Morges (CH); Stephane Hedarchet, Pully (CH)

(73) Assignee: Philip Morris Products S.A., Neuchatel (CH)

( * ) Notice: Subject to any disclaimer, the term of this patent is extended or adjusted under 35 U.S.C. 154(b) by 479 days.

(21) Appl. No.: 15/323,924

(22) PCT Filed: Jul. 10, 2015

(86) PCT No.: PCT/EP2015/065912
§ 371 (c)(1),
(2) Date: Jan. 4, 2017

(87) PCT Pub. No.: WO2016/005601
PCT Pub. Date: Jan. 14, 2016

(65) Prior Publication Data

US 2017/0143042 A1 May 25, 2017

(30) Foreign Application Priority Data

Jul. 11, 2014 (EP) .................................... 14176829

(51) Int. Cl.
*A24F 47/00* (2020.01)
*H05B 3/26* (2006.01)
*A61M 15/06* (2006.01)

(52) U.S. Cl.
CPC ............ *A24F 47/008* (2013.01); *H05B 3/26* (2013.01)

(58) Field of Classification Search
CPC ...... A24F 47/00; A24F 47/002; A24F 47/004; A24F 47/006; A24F 47/008; H05B 3/26; H05B 3/265; H02J 7/0009
See application file for complete search history.

(56) References Cited

U.S. PATENT DOCUMENTS 5,095,921 A 3/1992 Losee et al.
5,322,075 A 6/1994 Deevi et al.
(Continued)

FOREIGN PATENT DOCUMENTS

CN 202286300 U 7/2012
CN 103202540 A 7/2013
(Continued)

OTHER PUBLICATIONS

Combined Office Action and Search Report dated Oct, 29, 2018 in Russian Patent Application No. 2017104314/12 (with English translation), 10 pages.
(Continued)

*Primary Examiner* — Thor S Campbell
(74) *Attorney, Agent, or Firm* — Oblon, McClelland, Maier & Neustadt, L.L.P.

(57) ABSTRACT

An electrically operated aerosol-generating system is provided, including an aerosol-generating device, a removable aerosol-forming cartridge, and a removable heater provided separately from the cartridge. The cartridge includes at least one aerosol-forming substrate; the heater includes at least one electric heater element and first electrical contacts connected to the heater element; the device includes a main body defining a main cavity and at least one opening configured to receive the cartridge and the heater within the cavity, and an electric power supply and second electrical contacts connected thereto. When the cartridge and the heater are received within the cavity, the first and second electrical contacts contact each other and the heater is
(Continued)

configured to heat the substrate, the cartridge and the heater are substantially flat, and the cavity, the cartridge, and the heater are arranged so that the cartridge and the heater are substantially parallel and adjacent to each other.

14 Claims, 3 Drawing Sheets

(56) References Cited

U.S. PATENT DOCUMENTS

| | | | | |
|---|---|---|---|---|
| 5,388,594 | A | 2/1995 | Counts et al. | |
| 5,408,574 | A | 4/1995 | Deevi et al. | |
| 5,505,214 | A | 4/1996 | Collins et al. | |
| 5,591,368 | A | 1/1997 | Fleischhauer et al. | |
| 8,499,766 | B1 | 8/2013 | Newton | |
| 2005/0016550 | A1 | 1/2005 | Katase | |
| 2014/0060554 | A1* | 3/2014 | Collett | H05B 3/265<br>131/328 |
| 2015/0027459 | A1 | 1/2015 | Collett et al. | |

FOREIGN PATENT DOCUMENTS

| | | | |
|---|---|---|---|
| CN | 103859606 | A | 6/2014 |
| EP | 0 857 431 | A1 | 8/1998 |
| EP | 1 736 062 | A2 | 12/2006 |
| EP | 2 110 033 | A1 | 10/2009 |
| JP | 7-147965 | | 6/1995 |
| JP | 2010-104310 | | 5/2010 |
| RU | 110 608 | U1 | 11/2011 |
| RU | 132 318 | U1 | 9/2013 |
| WO | WO 2007/024130 | A1 | 3/2007 |
| WO | WO 2007/086374 | A1 | 6/2007 |
| WO | WO 2007/131449 | A1 | 11/2007 |
| WO | WO 2007/131450 | A1 | 11/2007 |
| WO | WO 2010/045670 | A1 | 4/2010 |
| WO | WO 2010/045671 | A1 | 4/2010 |
| WO | WO 2011/109848 | A1 | 9/2011 |
| WO | WO 2011/109849 | A1 | 9/2011 |
| WO | WO 2012/106739 | A1 | 8/2012 |
| WO | WO 2013/013808 | A1 | 1/2013 |
| WO | WO 2013/057185 | A1 | 4/2013 |
| WO | WO 2013/148810 | A1 | 10/2013 |
| WO | WO 2014/060269 | A1 | 4/2014 |
| WO | WO2014/061477 | | 4/2014 |
| WO | WO 2016/005602 | A1 | 1/2016 |

OTHER PUBLICATIONS

Extended European Search Report dated Jan. 12, 2015 in Patent Application No. 14 176 829.1.

International Search Report and Written Opinion of the International Searching Authority dated Sep. 25, 2015 in PCT/EP2015/065912 filed Jul. 10, 2015.

Chinese Office Action and Search Report with English translation dated Sep. 12, 2019 in corresponding Chinese Application No. 201580033317.8, (15 pages).

Japanese Office Action with English transiation dated Sep. 12, 2010 in corresponding Japanese Patent Application No. 2016-572437, (12 pages).

Combined Chinese Office Action and Search Report dated Jan. 23. 2019 in Chinese Patent Application No. 201580033317.8 (with English translation), 15 pages.

* cited by examiner

AEROSOL-GENERATING SYSTEM COMPRISING A REMOVABLE HEATER

The present invention relates to an aerosol-generating system comprising a removable heater. The present invention finds particular application as an aerosol-generating system for heating a nicotine-containing aerosol-forming substrate.

One type of aerosol-generating system is an electrically operated smoking system. Handheld electrically operated smoking systems consisting of an electric heater, an aerosol-generating device comprising a battery and control electronics, and an aerosol-forming cartridge are known. In some examples, the electric heater forms part of the aerosol-generating device. However, the electric heater may become contaminated with material from the aerosol-forming substrate during use and cleaning the electric heater inside the device can be difficult. In some cases, it may be necessary to dispose of the entire device if the heater cannot be adequately cleaned. Other examples attempt to overcome this problem by incorporating the electric heater into the aerosol-forming cartridge, so that the electric heater is disposed with the cartridge after use. However, although this eliminates the need for cleaning the heater, the cost of manufacturing the system increases significantly as it is necessary to incorporate a heater into every cartridge.

Accordingly, it would be desirable to produce an electrically operated aerosol-generating system that addresses the issue of heater contamination while minimising the cost of manufacturing the device and the cartridges.

According to the present invention there is provided an electrically operated aerosol-generating system comprising an aerosol-generating device, a removable aerosol-forming cartridge and a removable heater, wherein the removable aerosol-forming cartridge and the removable heater are provided separately from each other. The aerosol-forming cartridge comprises at least one aerosol-forming substrate, and the heater comprises at least one electric heater element and first electrical contacts connected to the at least one electric heater element. The aerosol-generating device comprises a main body defining a main cavity and at least one opening for receiving the aerosol-forming cartridge and the heater within the main cavity. The aerosol-generating device also comprises an electric power supply and second electrical contacts connected to the electric power supply. When the aerosol-forming cartridge and the heater are both received within the main cavity, the first electrical contacts are in contact with the second electrical contacts and the heater is arranged to heat the aerosol-forming substrate. The aerosol-forming cartridge and the heater are substantially flat, and the main cavity, the aerosol-forming cartridge and the heater are arranged such that the aerosol-forming cartridge and the heater are substantially parallel and adjacent to each other when received together in the main cavity.

As used herein, the term "aerosol-generating system" refers to the combination of an aerosol-generating device, an aerosol-forming cartridge and a heater, as further described and illustrated herein. In the system, the device, the cartridge and the heater cooperate to generate an aerosol.

As used herein, the term "aerosol-generating device" refers to a device that interacts with an aerosol-forming cartridge and a heater to generate an aerosol. The aerosol-generative device includes an electric power supply to operate the heater for heating the aerosol-forming cartridge.

As used herein, the term "cartridge" refers to a consumable article which is configured to coupled to an aerosol-generating device and which is assembled as a single unit that can be coupled and uncoupled as a single unit.

As used herein, the term "aerosol-forming cartridge" refers to a cartridge comprising at least one aerosol-forming substrate that is capable of releasing volatile compounds that can form an aerosol. For example, an aerosol-forming cartridge may be a smoking article that generates an aerosol.

As used herein, the term 'aerosol-forming substrate' is used to describe a substrate capable of releasing volatile compounds, which can form an aerosol. The aerosols generated from aerosol-forming substrates of aerosol-forming cartridges according to the invention may be visible or invisible and may include vapours (for example, fine particles of substances, which are in a gaseous state, that are ordinarily liquid or solid at room temperature) as well as gases and liquid droplets of condensed vapours.

As used herein, the term "substantially flat" refers to a component having a thickness to width ratio of at least 1:2. Preferably, the thickness to width ratio is less than about 1:20 to minimise the risk of bending or breaking the component.

Advantageously, providing a substantially flat heater and a substantially flat cartridge facilitates insertion of the heater and the cartridge into the device. Furthermore, flat components can be easily handled during manufacture. In addition, it has been found that aerosol release from the aerosol-forming substrate is improved when it is substantially flat and when arranged so that a flow of air is drawn across the width, length, or both, of the aerosol-forming substrate.

Arranging the main cavity, the heater and the cartridge so that the cartridge and the heater are substantially parallel and adjacent to each other when received together in the main cavity advantageously ensures optimum contact between the heater and the cartridge and therefore maximises the transfer of heat from the heater to the cartridge. This arrangement can also minimise the size of the cavity and therefore minimise the overall size of the aerosol-generating system.

By providing the heater as an element that is separate and removable from both the aerosol-generating device and the aerosol-forming cartridge, systems according to the present invention also facilitate cleaning of the heater in the event that the heater becomes contaminated with material from the aerosol-forming substrate. Furthermore, the heater can be used with multiple aerosol-forming cartridges and therefore makes the system more cost effective when compared to known systems in which each disposable cartridge comprises a heater element. Additionally, if necessary, the heater in systems according to the present invention can be replaced by the user without the need to replace the aerosol-generating device. Therefore, it is also possible to use multiple different heaters to heat multiple different aerosol-forming articles using only a single aerosol-generating device.

In preferred embodiments, the heater can be used to heat at least 5 aerosol-forming cartridges, more preferably at least 10 aerosol-forming cartridges, more preferably at least 15 aerosol-forming cartridges, most preferably at least 20 aerosol-forming cartridges. Additionally, or alternatively, the heater can be used to heat no more than 30 aerosol-forming cartridges, preferably no more than 25 aerosol-forming cartridges, most preferably no more than 20 aerosol-forming cartridges. In some embodiments, the aerosol-generating device is configured to monitor the number of aerosol-forming articles that have been heated by a particular heater. In these embodiments, the device may be configured to prompt the user to clean or replace the heater after a predetermined number of heating cycles. Additionally, or alternatively, the device may be configured to prevent further operation of the device until the heater has been removed for cleaning or replaced. The heater may comprise a data storage device so that the aerosol-generating device can maintain a record of the number of heating cycles for which a particular heater has been used, even if the heater is removed from the device and reinserted. The record may be recorded on the data storage device on the heater. Alternatively, the data storage device on the heater may comprise a unique data set that can be used by the aerosol-generating device to identify and distinguish between different heaters, and the aerosol-generating device may include a second data storage device for recording the number of heating cycles for each heater that is used with the device.

In any of the embodiments described above, the heater and the aerosol-forming cartridge may be configured to be removably connected to each other to form an aerosol-forming heater assembly. In these embodiments, the main cavity and the at least one opening are configured to receive the aerosol-forming heater assembly. This arrangement, in which the heater and the aerosol-forming cartridge are combined before insertion into the device, may be particularly advantageous in those embodiments in which at least one of the heater and the aerosol-forming cartridge is relatively thin. Specifically, since the combination of the heater and the aerosol-forming cartridge has a larger thickness than each of the components individually, inserting both the heater and the cartridge into the device as a single assembly may reduce the risk of bending or otherwise damaging at least one of the heater and the cartridge.

In those embodiments in which the heater and the aerosol-forming cartridge can be removably connected to each other to form an aerosol-forming heater assembly, the heater may comprise a heating cavity for removably receiving the aerosol-forming cartridge such that the aerosol-forming cartridge is at least partially within the heating cavity when the aerosol-forming cartridge and the heater are removably connected to each other. Utilising a heating cavity into which the cartridge is inserted can facilitate a secure connection between the cartridge and the heater. Using a heating cavity can also optimise the heat transfer from the heater to the aerosol-forming substrate during operation of the system.

Additionally, the heating cavity may also form an airflow cavity in which the aerosol-forming substrate is positioned when the cartridge is connected to the heater. The airflow cavity may form an airflow channel between an air inlet and an air outlet, wherein the air flow channel is configured to control the air flow through the aerosol-generating system. For example, an inner wall surface of the air flow channel may comprise one or more flow disturbing devices configured to generate a turbulent boundary layer air flow when air is drawn through the airflow channel.

In any of the embodiments described above in which the heater and the aerosol-forming cartridge can be removably connected to each other to form an aerosol-forming heater assembly, the at least one opening may be a single opening, wherein at least one of the opening and the main cavity comprises at least one of a guide slot, a groove, a rail, or a protrusion for guiding the aerosol-forming heater assembly into its correct position within the main cavity.

As an alternative to a heater and an aerosol-forming cartridge that can be removably connected to each other to form an aerosol-forming heater assembly, the at least one opening and the main cavity may be configured to separately receive both the heater and the aerosol-forming cartridge. That is, the device can receive both the heater and the cartridge at the same time, but each of the heater and the cartridge can be independently inserted into and removed from the device. Advantageously, this arrangement eliminates the need to remove and re-insert the heater each time the aerosol-forming cartridge is replaced. Instead, the heater can remain in the device for use with multiple aerosol-forming cartridges until it becomes necessary to remove the heater for cleaning or replacement.

In those embodiments in which the heater and the aerosol-forming cartridge can be independently inserted into and removed from the aerosol-generating device, at least one of the main cavity and the at least one opening preferably comprises at least one of a guide slot, a groove, a rail, or a protrusion for guiding each of the aerosol-forming cartridge and the heater into the correct positions within the main cavity.

Additionally, or alternatively, the at least one opening may comprise a first slot for receiving the aerosol-forming cartridge and a second slot for receiving the heater. In these embodiments, preferably the first and second slots, the heater and the aerosol-forming cartridge are each sized so that the aerosol-forming cartridge can be inserted only into the first slot and the heater can be inserted only into the second slot. Such an arrangement therefore prevents a user from inserting one or both of the aerosol-forming cartridge and the heater into the incorrect slot on the device, which may otherwise cause damage to at least one of the device, the heater and the aerosol-forming cartridge. For example, the first slot and the aerosol-forming cartridge may each comprise a maximum width and a maximum height, and the second slot and the heater may each comprise a maximum width that is larger than the maximum width of the first slot and the aerosol-forming cartridge, and the second slot and the heater may each comprise a maximum height that is smaller than the maximum height of the first slot and the aerosol-forming cartridge.

Additionally, the aerosol-generating system may comprise an electronic means for determining whether the heater and the cartridge have been inserted into the correct slots on the device. For example, the device may be configured to measure an electrical load on the component inserted into each of the first and second slots. Based on the measured electrical load, the device can determine whether the heater and the cartridge have been inserted into the correct slots. In the event that the heater and the cartridge have been inserted into the incorrect slots, the device is preferably configured so that it cannot be activated. Preferably, the device comprises and indicator for notifying the user that the heater and the cartridge have been inserted into the incorrect slots.

In any of the embodiments described above, at least one of the aerosol-forming cartridge, the heater and the aerosol-generating device may further comprise an additional heater arranged to heat at least part of the aerosol-forming substrate when the aerosol-forming cartridge and the heater are both received within the main cavity. In these embodiments, the additional heater may be connected to third electrical contacts, wherein the aerosol-generating device further comprises fourth electrical contacts connected to the electric power supply, the third and fourth electrical contacts being in contact with each other when the aerosol-forming cartridge and the heater are both received within the main cavity.

In some embodiments, the heater may form a primary heater and the additional heater may form a secondary, or boost heater. That is, the primary heater may heat the aerosol-forming substrate to a first temperature, and the additional heater may provide selective additional heat input to selectively raise the aerosol-forming substrate to a higher, second temperature. For example, the aerosol-generating device may be configured to function with two or more different types of aerosol-forming cartridge each comprising a different aerosol-forming substrate requiring a different heating profile. In these embodiments, the additional heater may be configured to heat the aerosol-generating substrate to the higher, second temperature only when certain types of aerosol-forming cartridge are inserted in the device. Alternatively, the additional heater may be selectively activated by the user during operation of the device to provide a temporary increase in the amount of aerosol delivered to the user.

Alternatively, the at least one aerosol-forming substrate on each aerosol-forming cartridge may comprise two or more aerosol-forming substrates, wherein the heater and the additional heater are arranged as sequential heaters to sequentially heat the different aerosol-forming substrates to provide a consistent aerosol delivery over the entire duration of operation of the system.

In some embodiments, the at least one electric heater element comprises a first electric heater element connected to the first electrical contacts, and the additional heater comprises a second electric heater element provided in the heater and connected to the third electrical contacts, wherein the first and second electric heater elements are arranged to heat different portions of the aerosol-forming cartridge when the aerosol-forming cartridge and the heater are both received within the main cavity. This arrangement is particularly suited to aerosol-forming cartridges comprising two or more aerosol-forming substrates, as described above.

In any of the embodiments described above, the heater may comprise an electrically insulating substrate, wherein the at least one electric heater element comprises one or more substantially flat heater elements arranged on the electrically insulating substrate. The substrate may be flexible. The substrate may be polymeric. The substrate may be a multi-layer polymeric material. The heating element, or heating elements, may extend across one or more apertures in the substrate.

In use, the heater may be arranged to heat the aerosol-forming substrate by one or more of conduction, convection and radiation. The heater may heat the aerosol-forming substrate by means of conduction and may be at least partially in contact with the aerosol-forming substrate. Alternatively, or in addition, the heat from the heater may be conducted to the aerosol-forming substrate by means of an intermediate heat conductive element. Alternatively, or in addition, the heater may transfer heat to the incoming ambient air that is drawn through or past the cartridge during use, which in turn heats the aerosol-forming substrate by convection.

The heater may comprise an internal electric heating element for at least partially inserting into the aerosol-forming substrate. An "internal heating element" is one which is suitable for insertion into an aerosol-forming material. Alternatively or additionally, the electric heater may comprise an external heating element. The term "external heating element" refers to one that at least partially surrounds the aerosol-forming cartridge. The heater may comprise one or more internal heating elements and one or more external heating elements. The heater may comprise a single heating element. Alternatively, the heater may comprise more than one heating element.

The at least one heating element may comprise an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal® and iron-manganese-aluminium based alloys. In composite materials, the electrically resistive material may optionally be embedded in, encapsulated or coated with an insulating material or vice-versa, depending on the kinetics of energy transfer and the external physicochemical properties required. Alternatively, the heater may comprise an infra-red heating element, a photonic source, or an inductive heating element.

The heater may take any suitable form. For example, the heater may take the form of a heating blade. Alternatively, the heater may take the form of a casing or substrate having different electro-conductive portions, or an electrically resistive metallic tube. Alternatively, the heater may comprise one or more heating needles or rods that run through the centre of the aerosol-forming substrate. Alternatively, the heater may be a disk (end) heater or a combination of a disk heater with heating needles or rods. The heater may comprise one or more stamped portions of electrically resistive material, such as stainless steel. Other alternatives include a heating wire or filament, for example a Ni—Cr (Nickel-Chromium), platinum, tungsten or alloy wire or a heating plate.

In certain preferred embodiments, the heater comprises a plurality of electrically conductive filaments. The plurality of electrically conductive filaments may form a mesh or array of filaments or may comprise a woven or non-woven fabric.

The electrically conductive filaments may define interstices between the filaments and the interstices may have a width of between 10 μm and 100 μm. Preferably the filaments give rise to capillary action in the interstices, so that when the heater is placed in contact with a liquid-containing aerosol-forming substrate, liquid to be vapourised is drawn into the interstices, increasing the contact area between the heater assembly and the liquid. The electrically conductive filaments may form a mesh of size between 160 and 600 Mesh US (+/−10 percent) (i.e. between 160 and 600 filaments per inch (+/−10 percent). The width of the interstices is preferably between 25 μm and 75 μm. The percentage of open area of the mesh, which is the ratio of the area of the interstices to the total area of the mesh, is preferably between 25 percent and 56 percent. The mesh may be formed using different types of weave or lattice structures. The mesh, array or fabric of electrically conductive filaments may also be characterised by its ability to retain liquid, as is well understood in the art. The electrically conductive filaments may have a diameter of between 10 μm and 100 μm, preferably between 8 μm and 50 μm, and more preferably between 8 μm and 39 μm. The filaments may have a round cross section or may have a flattened cross-section. The heater filaments may be formed by etching a sheet material, such as a foil. This may be particularly advantageous when the heater comprises an array of parallel filaments. If the heater comprises a mesh or fabric of filaments, the filaments may be individually formed and knitted together. The electrically conductive filaments may be provided as a mesh, array or fabric. The area of the mesh, array or fabric of electrically conductive filaments may be small, preferably less than or equal to 25 square millimetres, allowing it to be incorporated in to a handheld system. The mesh, array or fabric of electrically conductive filaments may, for example, be rectangular and have dimensions of 5 mm by 2 mm. Preferably, the mesh or array of electrically conductive filaments covers an area of between 10 percent and 50 percent of the area of the heater. More preferably, the mesh or array of electrically conductive filaments covers an area of between 15 percent and 25 percent of the area of the heater.

In one embodiment, electric energy is supplied to the electric heater until the heating element or elements of the electric heater reach a temperature of between approximately 180 degrees Celsius and about 310 degrees Celsius. Any suitable temperature sensor and control circuitry may be used in order to control heating of the heating element or elements to reach the required temperature. This is in contrast to conventional cigarettes in which the combustion of tobacco and cigarette wrapper may reach 800 degrees Celsius.

Preferably, the minimum distance between the electric heater and the at least one aerosol-forming substrate is less than 50 micrometres, preferably the cartridge comprises one or more layers of capillary fibres in the space between the electric heater and the aerosol-forming substrate.

The heater may comprise one or more heating elements above the at least one aerosol-forming substrate. Alternatively, the heater may comprise one or more heating elements below the at least one aerosol-forming substrate. With this arrangement, heating of the aerosol-forming substrate and aerosol release occur on opposite sides of the aerosol-forming cartridge. This has been found to be particularly effective for aerosol-forming substrates which comprise a tobacco-containing material. In certain embodiments, the heater comprises one or more heating elements positioned adjacent to opposite sides of the aerosol-forming substrate. Preferably the heater comprises a plurality of heating elements arranged to heat a different portion of the aerosol-forming substrate. In certain preferred embodiments, the at least one aerosol-forming substrate comprises a plurality of aerosol-forming substrates arranged separately on a base layer and the heater comprises a plurality of heating elements each arranged to heat a different one of the plurality of aerosol-forming substrates.

In any of the embodiments described above, the at least one aerosol-forming substrate may comprise nicotine. For example, the at least one aerosol-forming substrate may comprise a tobacco-containing material with volatile tobacco flavour compounds which are released from the aerosol-forming substrate upon heating.

Preferably, the at least one aerosol-forming substrate comprises an aerosol former, that is, a substance which generates an aerosol upon heating. The aerosol former may be, for instance, a polyol aerosol former or a non-polyol aerosol former. It may be a solid or liquid at room temperature, but preferably is a liquid at room temperature. Suitable polyols include sorbitol, glycerol, and glycols like propylene glycol or triethylene glycol. Suitable non-polyols include monohydric alcohols, such as menthol, high boiling point hydrocarbons, acids such as lactic acid, and esters such as diacetin, triacetin, triethyl citrate or isopropyl myristate. Aliphatic carboxylic acid esters such as methyl stearate, dimethyl dodecanedioate and dimethyl tetradecanedioate can also be used as aerosol formers. A combination of aerosol formers may be used, in equal or differing proportions. Polyethylene glycol and glycerol may be particularly preferred, whilst triacetin is more difficult to stabilise and may also need to be encapsulated in order to prevent its migration within the product. The at least one aerosol-forming substrate may include one or more flavouring agents, such as cocoa, liquorice, organic acids, or menthol.

The at least one aerosol-forming substrate may comprise a solid substrate. The solid substrate may comprise, for example, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco and expanded tobacco. Optionally, the solid substrate may contain additional tobacco or non-tobacco volatile flavour compounds, to be released upon heating of the substrate. Optionally, the solid substrate may also contain capsules that, for example, include the additional tobacco or non-tobacco volatile flavour compounds. Such capsules may melt during heating of the solid aerosol-forming substrate. Alternatively, or in addition, such capsules may be crushed prior to, during, or after heating of the solid aerosol-forming substrate.

Where the at least one aerosol-forming substrate comprises a solid substrate comprising homogenised tobacco material, the homogenised tobacco material may be formed by agglomerating particulate tobacco. The homogenised tobacco material may be in the form of a sheet. The homogenised tobacco material may have an aerosol-former content of greater than 5 percent on a dry weight basis. The homogenised tobacco material may alternatively have an aerosol former content of between 5 percent and 30 percent by weight on a dry weight basis. Sheets of homogenised tobacco material may be formed by agglomerating particulate tobacco obtained by grinding or otherwise comminuting one or both of tobacco leaf lamina and tobacco leaf stems; alternatively, or in addition, sheets of homogenised tobacco material may comprise one or more of tobacco dust, tobacco fines and other particulate tobacco by-products formed during, for example, the treating, handling and shipping of tobacco. Sheets of homogenised tobacco material may comprise one or more intrinsic binders, that is tobacco endogenous binders, one or more extrinsic binders, that is tobacco exogenous binders, or a combination thereof to help agglomerate the particulate tobacco. Alternatively, or in addition, sheets of homogenised tobacco material may comprise other additives including, but not limited to, tobacco and non-tobacco fibres, aerosol-formers, humectants, plasticisers, flavourants, fillers, aqueous and non-aqueous solvents and combinations thereof. Sheets of homogenised tobacco material are preferably formed by a casting process of the type generally comprising casting a slurry comprising particulate tobacco and one or more binders onto a conveyor belt or other support surface, drying the cast slurry to form a sheet of homogenised tobacco material and removing the sheet of homogenised tobacco material from the support surface.

Optionally, the solid substrate may be provided on or embedded in a thermally stable carrier. The carrier may take the form of powder, granules, pellets, shreds, spaghettis, strips or sheets. Alternatively, the carrier may be a tubular carrier having a thin layer of the solid substrate deposited on its inner surface, such as those disclosed in U.S. Pat. Nos. 5,505,214, 5,591,368 and 5,388,594, or on its outer surface, or on both its inner and outer surfaces. Such a tubular carrier may be formed of, for example, a paper, or paper like material, a non-woven carbon fibre mat, a low mass open mesh metallic screen, or a perforated metallic foil or any other thermally stable polymer matrix. The solid substrate may be deposited on the surface of the carrier in the form of, for example, a sheet, foam, gel or slurry. The solid substrate may be deposited on the entire surface of the carrier, or alternatively, may be deposited in a pattern in order to provide a predetermined or non-uniform flavour delivery during use. Alternatively, the carrier may be a non-woven fabric or fibre bundle into which tobacco components have been incorporated, such as that described in EP-A-0 857 431. The non-woven fabric or fibre bundle may comprise, for example, carbon fibres, natural cellulose fibres, or cellulose derivative fibres.

As an alternative to a solid tobacco-based aerosol-forming substrate, the at least one aerosol-forming substrate may comprise a liquid substrate and the cartridge may comprise means for retaining the liquid substrate, such as one or more containers. Alternatively or in addition, the cartridge may comprise a porous carrier material, into which the liquid substrate is absorbed, as described in WO-A-2007/024130, WO-A-2007/066374, EP-A-1 736 062, WO-A-2007/131449 and WO-A-2007/131450.

The liquid substrate is preferably a nicotine source comprising one or more of nicotine, nicotine base, a nicotine salt, such as nicotine-HCl, nicotine-bitartrate, or nicotine-ditartrate, or a nicotine derivative.

The nicotine source may comprise natural nicotine or synthetic nicotine.

The nicotine source may comprise pure nicotine, a solution of nicotine in an aqueous or non-aqueous solvent or a liquid tobacco extract.

The nicotine source may further comprise an electrolyte forming compound. The electrolyte forming compound may be selected from the group consisting of alkali metal hydroxides, alkali metal oxides, alkali metal salts, alkaline earth metal oxides, alkaline earth metal hydroxides and combinations thereof.

For example, the nicotine source may comprise an electrolyte forming compound selected from the group consisting of potassium hydroxide, sodium hydroxide, lithium oxide, barium oxide, potassium chloride, sodium chloride, sodium carbonate, sodium citrate, ammonium sulfate and combinations thereof.

In certain embodiments, the nicotine source may comprise an aqueous solution of nicotine, nicotine base, a nicotine salt or a nicotine derivative and an electrolyte forming compound.

Alternatively or in addition, the nicotine source may further comprise other components including, but not limited to, natural flavours, artificial flavours and antioxidants.

In addition to a nicotine-containing aerosol-forming substrate, the aerosol-forming cartridge may further comprise a source of a volatile delivery enhancing compound that reacts with the nicotine in the gas phase to aid delivery of the nicotine to the user.

The volatile delivery enhancing compound may comprise a single compound.

Alternatively, the volatile delivery enhancing compound may comprise two or more different compounds.

Preferably, the volatile delivery enhancing compound is a volatile liquid.

The volatile delivery enhancing compound may comprise an aqueous solution of one or more compounds. Alternatively the volatile delivery enhancing compound may comprise a non-aqueous solution of one or more compounds.

The volatile delivery enhancing compound may comprise two or more different volatile compounds. For example, the volatile delivery enhancing compound may comprise a mixture of two or more different volatile liquid compounds.

Alternatively, the volatile delivery enhancing compound may comprise one or more non-volatile compounds and one or more volatile compounds. For example, the volatile delivery enhancing compound may comprise a solution of one or more non-volatile compounds in a volatile solvent or a mixture of one or more non-volatile liquid compounds and one or more volatile liquid compounds.

In one embodiment, the volatile delivery enhancing compound comprises an acid. The volatile delivery enhancing compound may comprise an organic acid or an inorganic acid. Preferably, the volatile delivery enhancing compound comprises an organic acid, more preferably a carboxylic acid, most preferably an alpha-keto or 2-oxo acid.

In a preferred embodiment, the volatile delivery enhancing compound comprises an acid selected from the group consisting of 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid and combinations thereof. In a particularly preferred embodiment, the volatile delivery enhancing compound comprises pyruvic acid.

As an alternative to a solid or liquid aerosol-forming substrate, the at least one aerosol-forming substrate may be any other sort of substrate, for example, a gas substrate, a gel substrate, or any combination of the various types of substrate described.

In any of the embodiments described above, the at least one aerosol-forming substrate may comprise a single aerosol-forming substrate. Alternatively, the at least one aerosol-forming substrate may comprise a plurality of aerosol-forming substrates. The plurality of aerosol-forming substrates may have the substantially the same composition. Alternatively, the plurality of aerosol-forming substrates may comprise two or more aerosol-forming substrates having substantially different compositions. The plurality of aerosol-forming substrates may be stored together on the base layer. Alternatively, the plurality of aerosol-forming substrates may be stored separately. By separately storing two or more different portions of aerosol-forming substrate, it is possible to store two substances which are not entirely compatible in the same cartridge. Advantageously, separately storing two or more different portions of aerosol-forming substrate may extend the life of the cartridge. It also enables two incompatible substances to be stored in the same cartridge. Further, it enables the aerosol-forming substrates to be aerosolised separately, for example by heating each aerosol-forming substrate separately. Thus, aerosol-forming substrates with different heating profile requirements can be heated differently for improved aerosol formation. It may also enable more efficient energy use, since more volatile substances can be separately from less volatile substances and to a lesser degree. Separate aerosol-forming substrates can also be aerosolised in a predefined sequence, for example by heating a different one of the plurality of aerosol-forming substrates for each use, ensuring a 'fresh' aerosol-forming substrate is aerosolised each time the cartridge is used. In those embodiments comprising a liquid nicotine aerosol-forming substrate and a volatile delivery enhancing compound aerosol-forming substrate, the nicotine and the volatile delivery enhancing compound are advantageously stored separately and reacted together in the gas phase only when the system is in operation.

Preferably the at least one aerosol-forming substrate is substantially flat. The at least one aerosol-forming substrate may have any suitable cross-sectional shape. Preferably, the at least one aerosol-forming substrate has a non-circular cross-sectional shape. In certain preferred embodiments, the at least one aerosol-forming substrate has a substantially rectangular cross-sectional shape. In certain embodiments, the at least one aerosol-forming substrate has an elongate, substantially rectangular, parallelepiped shape.

In certain preferred embodiments, the at least one aerosol-forming substrate has a vaporisation temperature of from about 60 degrees Celsius to about 320 degrees Celsius, preferably from about 70 degrees Celsius to about 230 degrees Celsius, preferably from about 90 degrees Celsius to about 180 degrees Celsius. As used herein, the term 'vaporisation temperature' refers to the temperature at which.

The aerosol-forming cartridge may have any suitable size. Preferably, the cartridge has suitable dimensions for use with a handheld aerosol-generating device. In certain embodiments, the cartridge has length of from about 5 mm to about 200 mm, preferably from about 10 mm to about 100 mm, more preferably from about 20 mm to about 35 mm. In certain embodiments, the cartridge has width of from about 5 mm to about 12 mm, preferably from about 7 mm to about 10 mm. In certain embodiments, the cartridge has a height of from about 2 mm to about 10 mm, preferably from about 5 mm to about 8 mm.

In use, at least one of the aerosol-forming cartridge and the aerosol-generating device may be connected to a separate mouthpiece portion by which a user can draw a flow of air through or adjacent to the cartridge by sucking on a downstream end of the mouthpiece portion. In such embodiments, preferably, the cartridge is arranged such that the resistance to draw at a downstream end of the mouthpiece portion is from about 50 mmWG to about 130 mmWG, more preferably from about 80 mmWG to about 120 mmWG, more preferably from about 90 mmWG to about 110 mmWG, most preferably from about 95 mmWG to about 105 mmWG. As used herein, the term "resistance to draw" refers the pressure required to force air through the full length of the object under test at a rate of 17.5 ml/sec at 22° C. and 101 kPa (760 Torr). Resistance to draw is typically expressed in units of millimetres water gauge (mmWG) and is measured in accordance with ISO 6565:2011.

The heater comprises at least first electrical contacts arranged to supply power to the heater from the electric power supply in the aerosol-generating device. Additionally, the at least first electrical contacts may be arranged to transfer data to or from the heater, or both to and from the heater. The electrical contacts provided on the heater may be accessible from outside of the heater. The electrical contacts may be positioned along one or more edges of the heater. In certain embodiments, the electrical contacts may be positioned along a lateral edge of the heater. For example, the electrical contacts may be positioned along the upstream edge of the heater. Alternatively, or in addition, the electrical contacts may be positioned along a single longitudinal edge of the heater.

Additionally, the aerosol-forming cartridge may comprise one or more electrical contacts. The electrical contacts provided on the aerosol-forming cartridge may be accessible from outside of the cartridge. The electrical contacts may be positioned along one or more edges of the cartridge. In certain embodiments, the electrical contacts may be positioned along a lateral edge of the cartridge. For example, the electrical contacts may be positioned along the upstream edge of the cartridge. Alternatively, or in addition, the electrical contacts may be positioned along a single longitudinal edge of the cartridge. The electrical contacts on the cartridge may comprise data contacts for transferring data to or from the cartridge, or both to and from the cartridge.

Any of the electrical contacts described above may have any suitable form. The electrical contacts may be substantially flat. Advantageously, substantially flat electrical contacts have been found to be more reliable for establishing an electrical connection and are easier to manufacture. Preferably, the electrical contacts comprise part of a standardised electrical connection, including, but not limited to, USB-A, USB-B, USB-mini, USB-micro, SD, miniSD, or microSD type connections. Preferably, the electrical contacts comprise the male part of a standardised electrical connection, including, but not limited to, USB-A, USB-B, USB-mini, USB-micro, SD, miniSD, or microSD type connections. As used herein, the term "standardised electrical connection" refers an electrical connection which is specified by an industrial standard.

In any of the embodiments described above, the cartridge may comprise a cover layer fixed to a base layer and over at least part of the at least one aerosol-forming substrate. Advantageously, the cover layer may hold the at least one aerosol-forming substrate in place on the base layer. The cover layer may be fixed directly to the base layer, or indirectly via one or more intermediate layers or components. Aerosol released by the aerosol-forming substrate may pass through one or more apertures in the cover layer, base layer, or both. The cover layer may have at least one gas permeable window to allow aerosol released by the aerosol-forming substrate to pass through the cover layer. The gas permeable window may be substantially open. Alternatively, the gas permeable window may comprise a perforated membrane, or a grid extending across an aperture in the cover layer. The grid may be of any suitable form, such as a transverse grid, longitudinal grid, or mesh grid. The cover layer may form a seal with the base layer. The cover layer may form a hermetic seal with the base layer. The cover layer may comprise a polymeric coating at least where the cover layer is fixed to the base layer, the polymeric coating forming a seal between the cover layer and the base layer.

The aerosol-forming cartridge may comprise a protective foil positioned over at least part of the at least one aerosol-forming substrate. The protective foil may be gas impermeable. The protective foil may be arranged to hermetically seal the aerosol-forming substrate within the cartridge. As used herein, the term "hermetically seal" means that the weight of the volatile compounds in the aerosol-forming substrate changes by less than 2% over a two week period, preferably over a two month period, more preferably over a two year period.

The base layer may comprise at least one cavity in which the aerosol-forming substrate is held. In these embodiments, the protective foil may be arranged to close the one or more cavities. The protective foil may be at least partially removable to expose the at least one aerosol-forming substrate. Preferably, the protective foil is removable. Where the base layer comprises a plurality of cavities in which a plurality of aerosol-forming substrates are held, the protective foil may be removable in stages to selectively unseal one or more of the aerosol-forming substrate. For example, the protective foil may comprise one or more removable sections, each of which is arranged to reveal one or more of the cavities when removed from the remainder of the protective foil. Alternatively, or in addition, the protective foil may be attached such that the required removal force varies between the various stages of removal as an indication to the user. For example, the required removal force may increase between adjacent stages so that the user must deliberately pull harder on the protective foil to continue removing the protective foil. This may be achieved by any suitable means. For example, the pulling force may be varied by altering the type, quantity, or shape of an adhesive layer, or by altering the shape or amount of a weld line by which the protective foil is attached.

The protective foil may be removably attached to the base layer either directly or indirectly via one or more intermediate components. Where the cartridge comprises a cover layer as described above, the protective foil may be removably attached to the cover layer. Where the cover layer has one or more gas permeable windows, the protective foil may extend across and close the one or more gas permeable windows. The protective foil may be removably attached by any suitable method, for example using adhesive. The protective foil may be removably attached by ultrasonic welding. The protective foil may be removably attached by ultrasonic welding along a weld line. The weld line may be continuous. The weld line may comprise two or more continuous weld lines arranged side by side. With this arrangement, the seal can be maintained provided at least one of the continuous weld lines remains intact.

The protective foil may be a flexible film. The protective foil may comprise any suitable material or materials. For example, the protective foil may comprise a polymeric foil, for example Polypropylene (PP) or Polyethylene (PE). The protective foil may comprise a multilayer polymeric foil.

The aerosol-generating device may comprise a controller configured to control the supply of electrical power to the heater.

The electric power supply may be a DC voltage source. In preferred embodiments, the power supply is a battery. For example, the power supply may be a Nickel-metal hydride battery, a Nickel cadmium battery, or a Lithium based battery, for example a Lithium-Cobalt, a Lithium-Iron-Phosphate or a Lithium-Polymer battery. The power supply may alternatively be another form of charge storage device such as a capacitor. The power supply may require recharging and may have a capacity that allows for the storage of enough energy for use of the aerosol-generating device with one or more aerosol-generating articles.

The aerosol-generating device may comprise one or more temperature sensors configured to sense the temperature of at least one of the heater and the one or more aerosol-forming substrates. In such embodiments, the controller, where present, may be configured to control the supply of power to the heater based on the sensed temperature.

In those embodiments in which the heater comprises at least one resistive heating element, the at least one heater element may be formed using a metal having a defined relationship between temperature and resistivity. In such embodiments, the metal may be formed as a track between two layers of suitable insulating materials. A heater element formed in this manner may be used both as a heater and a temperature sensor.

In any of the embodiments described above, the aerosol-generating device may comprise an external plug or socket allowing the aerosol-generating device to be connected to another electrical device. For example, the aerosol-generating device may comprise a USB plug or a USB socket to allow connection of the aerosol-generating device to another USB enabled device. For example, the USB plug or socket may allow connection of the aerosol-generating device to a USB charging device to charge a rechargeable power supply within the aerosol-generating device. Additionally, or alternatively, the USB plug or socket may support the transfer of data to or from, or both to and from, the aerosol-generating device. For example, the device may be connected to a computer to download data from the device, such as usage data. Additionally, or alternatively, the device may be connected to a computer to transfer data to the device, such as new heating profiles for new or updated aerosol-forming cartridges, wherein the heating profiles are stored within a data storage device within the aerosol-generating device.

In those embodiments in which the device comprises a USB plug or socket, the device may further comprise a removable cover that covers the USB plug or socket when not in use. In embodiments in which the USB plug or socket is a USB plug, USB plug may additionally or alternatively be selectively retractable within the device.

The invention will now be further described, by way of example only, with reference to the accompanying drawings in which.

Figure 1:
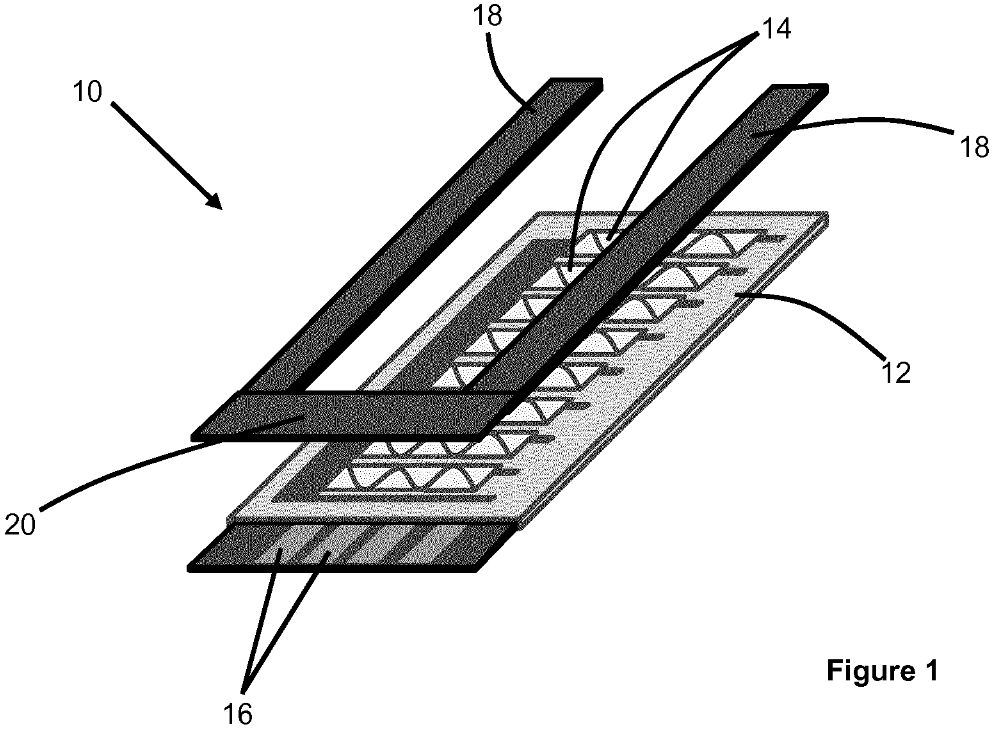
FIG. 1 shows a partially exploded view of a heater in accordance with an embodiment of the present invention.
Figure 2:
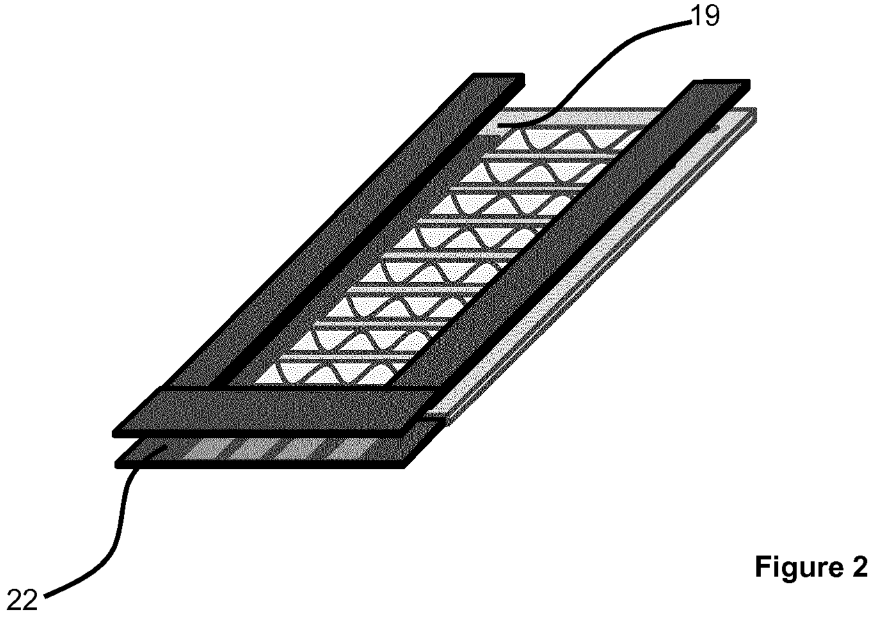
FIG. 2 shows the heater of FIG. 1 in a fully assembled configuration.

FIGS. 1 and 2 show a heater 10 in accordance with an embodiment of the present invention. The heater 10 comprises an electrically insulating substrate layer 12 on which multiple electric heater elements 14 are provided. Multiple electrical contacts 16 are also provided on the electrically insulating substrate layer 12 at an upstream end of the heater 10. The electrical contacts 16 provide power to the electric heater elements 14 when the heater 10 is connected to an aerosol-generating device.

The heater 10 further comprises a set of guide rails 18 that extend along the longitudinal edges of the heater 10 and an end stop 20 extending across the upstream lateral edge of the heater. The inner edge of each of the guide rails 18 extending along the longitudinal edges are spaced from the insulating substrate layer 12 to form longitudinal grooves 19 for receiving an aerosol-forming cartridge. The end stop 20 is spaced apart from the electrical contacts 16 to form a slot 22 into which the corresponding electrical contacts on an aerosol-generating device are received.

Figure 3:
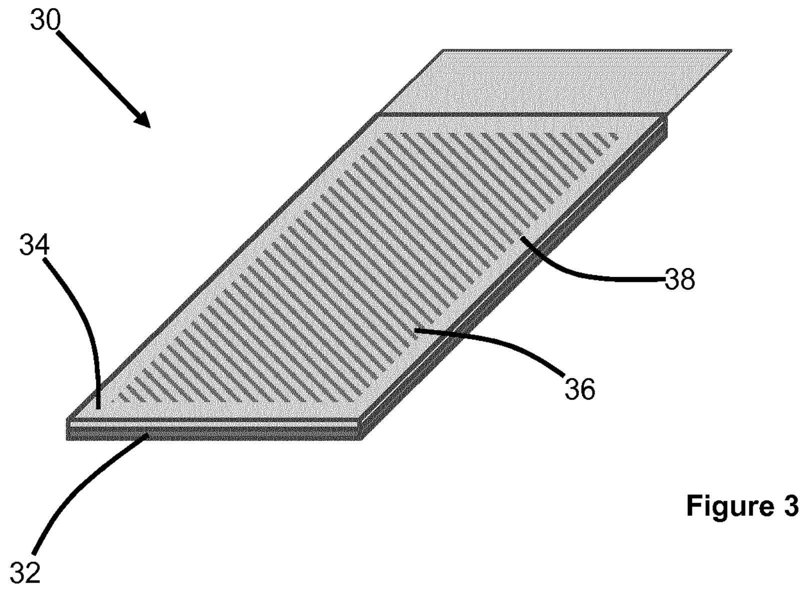
FIG. 3 shows an aerosol-forming cartridge in accordance with an embodiment of the present invention.

FIG. 3 shows an aerosol-forming cartridge 30 in accordance with an embodiment of the present invention. The cartridge 30 comprises a base layer 32 and a cover layer 34 overlying multiple aerosol-forming substrates sandwiched between the base layer 32 and the cover layer 34. The cover layer 34 comprises a mesh grid 36 overlying the aerosol-forming substrates to allow the aerosol particles to escape from the aerosol-forming cartridge 30 during heating. A removable polymeric film 38 overlies the mesh grid 36 to prevent premature escape of the volatile components from the aerosol-generating substrates. Before using the cartridge 30, the polymeric film 38 is removed.

Figure 4:
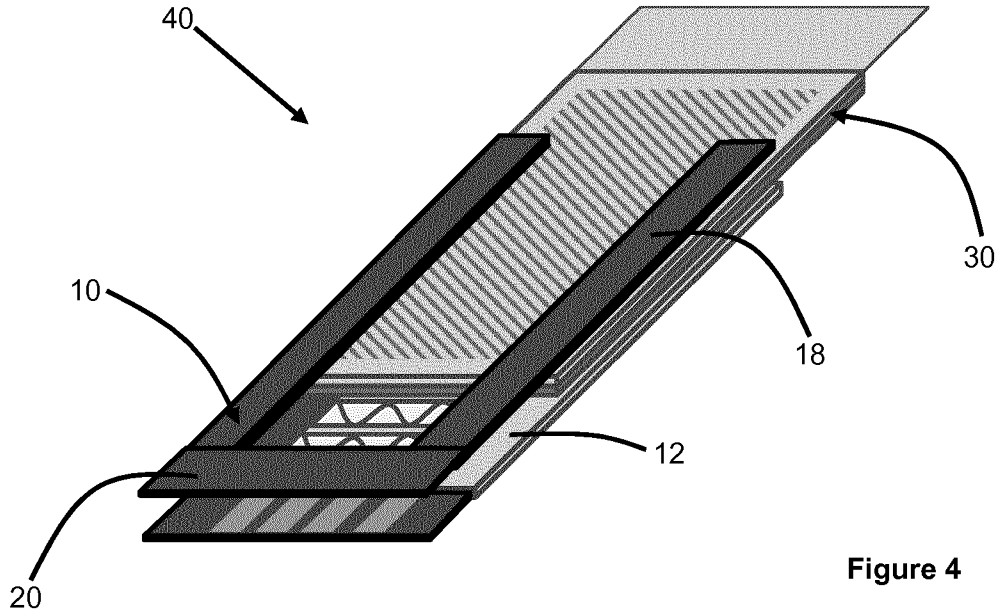
FIG. 4 shows the aerosol-forming cartridge of FIG. 3 inserted into the heater of FIG. 2 to form an aerosol-forming heater assembly.

FIG. 4 shows the aerosol-forming cartridge 30 of FIG. 3 inserted into the heater 10 of FIG. 2 to form an aerosol-forming heater assembly 40 in accordance with an embodiment of the present invention. The removable polymeric film 38 is removed from the cartridge 30 and the cartridge 30 is inserted into the longitudinal grooves 19 between the guide rails 18 and the insulating substrate layer 12 of the heater 10.

FIG. 4 shows the cartridge 30 partially inserted into the heater 10. Upon full insertion of the cartridge 30 into the heater 10, the cartridge 30 abuts the end stop 20.

Figure 5:
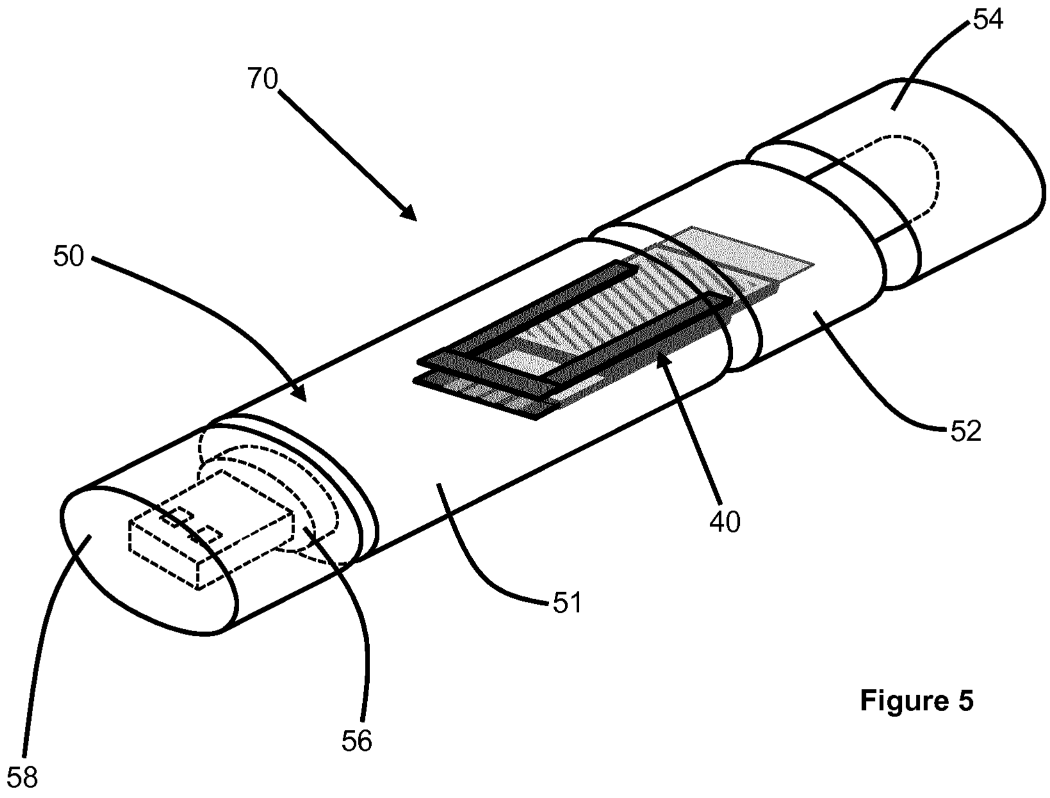
FIG. 5 shows the aerosol-forming heater assembly of FIG. 4 inserted into an aerosol-generating device to form an aerosol-generating system in accordance with an embodiment of the present invention.

FIG. 5 shows the aerosol-forming heater assembly 40 of FIG. 4 inserted into an aerosol generating device 50 to form an aerosol-generating system 70 in accordance with an embodiment of the present invention. The aerosol-generating device 50 comprises a main body 51 defining a main cavity for receiving the heater assembly 40 and an opening at a downstream end of the device 50 through which the heater assembly 40 is inserted into the main cavity. Fully inserting the heater assembly 40 into the device 50 contacts the multiple electrical contacts 16 on the heater 10 with multiple electrical contacts in the main cavity of the device 50. The electrical contacts conduct power to the heater elements 14 from a rechargeable battery within the device 50. A removable mouthpiece 52 is provided at an upstream end of the device 50, wherein the mouthpiece 52 is removed from the device 50 to allow insertion of the heater assembly 40 into the device 50, and the mouthpiece 52 is then reattached to the device 50 after the heater assembly 40 has been fully inserted. A removable mouthpiece cover 54 covers the mouthpiece 52 when the device 50 is not in use.

A USB plug 56 is provided at a downstream end of the device 50 for insertion into a suitable USB socket. The USB plug 56 can be used for charging the rechargeable battery within the device 50, as well as exchanging data with the device 50. For example, the USB plug can be used to download usage data from the device 50, as well as uploading new data to the device 50, such as new heating profiles. A removable cover 58 covers the USB plug 56 when the USB plug 56 is not in use.

The invention claimed is:

1. An electrically operated aerosol-generating system comprising an aerosol-generating device; a removable aerosol-forming cartridge, and a removable heater, the removable aerosol-forming cartridge and the removable heater being provided separately from each other, the removable aerosol-forming cartridge comprising at least one aerosol-forming substrate, the removable heater comprising at least one electric heater element and first electrical contacts connected to the at least one electric heater element, and the aerosol-generating device comprising:

a main body defining a main cavity and at least one opening configured to receive the removable aerosol-forming cartridge and the removable heater within the main cavity;

an electric power supply; and second electrical contacts connected to the electric power supply, wherein the removable heater and the removable aerosol-forming cartridge are configured to be removably connected to each other to form an aerosol-forming heater assembly, wherein the main cavity and the at least one opening are configured to receive the aerosol-forming heater assembly, wherein, when the removable aerosol-forming cartridge and the removable heater are both received within the main cavity, the first electrical contacts are in contact with the second electrical contacts and the removable heater is configured to heat the aerosol-forming substrate, wherein the removable aerosol-forming cartridge and the removable heater are substantially flat, wherein the main cavity, the removable aerosol-forming cartridge, and the removable heater are arranged such that the removable aerosol-forming cartridge and the removable heater are substantially parallel and adjacent to each other when received together in the main cavity, and wherein the removable heater further comprises a heating cavity configured to removably receive the aerosol-forming cartridge such that the aerosol-forming cartridge is at least partially received within the heating cavity when the aerosol-forming cartridge and the removable heater are removably connected to each other to form the aerosol-forming heater assembly.

2. The electrically operated aerosol-generating system according to claim 1, wherein the at least one opening is a single opening, and wherein at least one of the opening and the main cavity comprises at least one of a guide slot, a groove, a rail, or a protrusion, configured to guide the aerosol-forming heater assembly into a correct position within the main cavity.

3. The electrically operated aerosol-generating system according to claim 1, wherein the at least one opening and the main cavity are configured to separately receive both the removable heater and the aerosol-forming cartridge.

4. The electrically operated aerosol-generating system according to claim 3, wherein at least one of the main cavity and the at least one opening comprises at least one of a guide slot, a groove, a rail, or a protrusion, configured to guide each of the aerosol-forming cartridge and the removable heater into correct positions within the main cavity.

5. The electrically operated aerosol-generating system according to claim 3, wherein the at least one opening comprises a first slot configured to receive the aerosol-forming cartridge, and a second slot configured to receive the removable heater.

6. The electrically operated aerosol-generating system according to claim 5, wherein the first and second slots, the removable heater, and the aerosol-forming cartridge are each sized so that the aerosol-forming cartridge is insertable only into the first slot and the removable heater is insertable only into the second slot.

7. The electrically operated aerosol-generating system according to claim 1, wherein at least one of the aerosol-forming cartridge, the removable heater, and the aerosol-generating device further comprises an additional heater configured to heat at least part of the aerosol-forming substrate when the aerosol-forming cartridge and the removable heater are both received within the main cavity.

8. The electrically operated aerosol-generating system according to claim 7, wherein the additional heater is connected to third electrical contacts, and wherein the aerosol-generating device further comprises fourth electrical contacts connected to the electric power supply, the third and fourth electrical contacts being in contact with each other when the aerosol-forming cartridge and the removable heater are both received within the main cavity.

9. The electrically operated aerosol-generating system according to claim 8, wherein the at least one electric heater element comprises a first electric heater element connected to the first electrical contacts, wherein the additional heater comprises a second electric heater element provided in the additional heater and connected to the third electrical contacts, and wherein the first and second electric heater elements are configured to heat different portions of the aerosol-forming cartridge when the aerosol-forming cartridge and the removable heater are both received within the main cavity.

10. The electrically operated aerosol-generating system according to claim 1, wherein the removable heater comprises an electrically insulating substrate, and wherein the at least one electric heater element comprises one or more substantially flat heater elements arranged on the electrically insulating substrate.

11. The electrically operated aerosol-generating system according to claim 1, wherein the removable heater comprises a data storage medium configured to communicate with the aerosol-generating device when the removable heater is inserted into the main cavity.

12. The electrically operated aerosol-generating system according to claim 11, wherein the aerosol-generating device and the data storage medium are configured to store data on the data storage medium indicative of a number of heating cycles for which the removable heater has been used.

13. The electrically operated aerosol-generating system according to claim 1, wherein the aerosol-forming substrate comprises nicotine.

14. The electrically operated aerosol-generating system according to claim 1, wherein the removable aerosol-forming cartridge further comprises a plurality of layers.

* * * * *